United States Patent [19]
Bunker

[11] Patent Number: 5,304,585
[45] Date of Patent: Apr. 19, 1994

[54] DENTIN AND ENAMEL ADHESIVE

[75] Inventor: James E. Bunker, St. Paul, Minn.

[73] Assignee: Minnesota Mining and Manufacturing, St. Paul, Minn.

[21] Appl. No.: 940,051

[22] Filed: Sep. 3, 1992

Related U.S. Application Data

[60] Division of Ser. No. 500,683, Mar. 28, 1990, Pat. No. 5,177,121, which is a division of Ser. No. 328,753, Mar. 23, 1987, Pat. No. 4,929,746, which is a continuation of Ser. No. 33,520, Apr. 1, 1987, abandoned, which is a division of Ser. No. 665,960, Oct. 29, 1984, Pat. No. 4,669,983, which is a division of Ser. No. 234,560, Feb. 13, 1981, abandoned.

[51] Int. Cl.$^5$ ............................................. C08F 130/02
[52] U.S. Cl. ................................... 523/116; 523/118; 526/276; 526/277; 526/278
[58] Field of Search ................ 523/116, 118; 526/276, 526/277, 278

[56] References Cited

U.S. PATENT DOCUMENTS

| | | | |
|---|---|---|---|
| Re. 31,985 | 9/1985 | Hayashi et al. | 523/501 |
| 4,044,044 | 8/1977 | Saito | 260/47 |
| 5,063,257 | 11/1991 | Akabrene et al. | 523/116 |
| 5,089,051 | 2/1992 | Eppinger et al. | 523/116 |

FOREIGN PATENT DOCUMENTS

| | | |
|---|---|---|
| 753580 | 1/1971 | Belgium . |
| 1935630 | 12/1968 | Fed. Rep. of Germany . |
| 1903168 | 7/1970 | Fed. Rep. of Germany . |
| 2207183 | 9/1972 | Fed. Rep. of Germany . |
| 2344281 | 10/1977 | France . |
| 0166363 | 8/1985 | Japan . |
| 560226 | 3/1975 | Switzerland . |
| 572941 | 2/1976 | Switzerland . |

OTHER PUBLICATIONS

Journal of Gen. Chem., vol. 48, 1979, pp. 1788-1790, 1791-1796.

*Primary Examiner*—Paul R. Michl
*Assistant Examiner*—Andrew E. C. Merriam
*Attorney, Agent, or Firm*—Gary L. Griswold; Walter N. Kirn; Dale A. Bjorkman

[57] ABSTRACT

Organic esters of chlorine-containing or bromine-containing phosphorus acids and BIS-GMA, and organic esters of phosphorus acids having chlorine or bromine bonded directly to phosphorus (are described), the organic radical of said esters containing at least one polymerizable functional group. Also described are dental line, restorative, composite, and adhesive compositions containing such organic esters, as well as methods for using such compositions to repair or veneer dental tissue.

9 Claims, No Drawings

DENTIN AND ENAMEL ADHESIVE

TECHNICAL FIELD

This is a division of application Ser. No. 07/500,683 filed Mar. 28, 1990 (now U.S. Pat. No. 5,177,121), which is in turn a division of application Ser. No. 07/328,753 filed Mar. 23, 1987 (now U.S. Pat. No. 4,929,746), which is in turn a continuation of application Ser. No. 07/033,520 filed Apr. 1, 1987 (now abandoned), which is in turn a division of application Ser. No. 06/665,960 filed Oct. 29, 1984 (now U.S. Pat. No. 4,669,983), which is in turn a division of application Ser. No. 06/234,560 filed Feb. 13, 1981 (now abandoned).

This invention relates to the field of polymerizable compounds. In addition, this invention relates to compositions for use as liners, restoratives, and composites for the repair of teeth, compositions for use in fastening orthodontic brackets or crowns to teeth, and to a method for preparing such compositions. This invention also relates to a method for repairing adhering, or altering the position of teeth, through the use of such compositions as liners, restoratives, composites, and adhesives.

BACKGROUND ART

Practitioners in the field of dentistry have long sought polymerizable compositions which would adhere well to dentin. One of the first attempts at bonding to dentin was recorded by Buonocore et al, utilizing a polymerizable mixture containing glycerophosphate dimethacrylate (I):

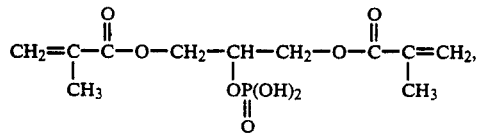

see M. Buonocore, W. Wileman, and F. Brudevold, *J. Dent. Res.*, 35, 846 (1956), and M. Buonocore and M. Quigley, *J. Amer. Dent. Assoc.*, 57, 807 (1958).

Anbar et al have reported dentin adhesives containing vinyl phosphonic acid (II) or vinylbenzyl phosphonic acid (III):

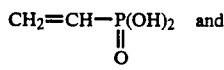

see M. Anbar and E. Farley, *J. Dent. Res.*, 53, 879 (1974) and E. Farley, R. Jones, and M. Anbar, *J. Dent. Res.*, 56, 943 (1977).

Various phosphoric acid and phosphonic acid esters have been described as having good adhesion to dentin in patent applications and patents, see, e.g., U.S. Pat. Nos. 4,182,035, 4,222,780, and 4,235,633, O.L.S. No. 2711234, and Japanese laid-open application Nos. 77-113089, 78-30193, 78-39331, 78-67740, 78-69494, 78-110637, 78-113843, 78-134037, 78-144939, 78-138441, 79-21438, and 79-28339. Also, there has been introduced in Japan a dental liner composition, under the name "Clearfil", utilizing a two-part resin system. The first (catalyst) portion of such resin system contains a polymerizable phosphoric acid of undetermined structure. The second (universal) part of such resin system contains an ethanolic solution of sodium benzene sulfinate and N,N-dihydroxyethyl-p-toluidine (the latter compound will be referred to hereafter as "DHPT"). It has been recommended that the use of this composition be preceeded by acid etching of the exposed dentin (e.g., with ortho-phosphoric acid) prior to application of the liner composition. However, the long term physiological affects of such acid etching are unknown, and the efficacy of acid etching of dentin has been questioned by practitioners, see, e.g., M.G. Buonocore, "The Challenge of Bonding to Dentin", *The Acid Etch Technique*, L. M. Silverstone and I. L. Dogon, Eds., Proceedings of an International Symposium at St. Moritz, Switzerland, Dec. 16–18, 1974, North Central Publishing Co. (St. Paul, 1975). Also, acid etching is a somewhat difficult procedure to carry out, since the highly corrosive acid is injurious to the soft tissues of the mouth. In addition, commercial products containing ortho-phosphoric acid are, in some jurisdictions, subjected to special transportation requirements which increase the costs of shipping dental supplies (e.g. restoration kits) which contain vials of ortho-phosphoric acid.

A non-phosphorus acid compound which is said to possess bonding capability to dentin is reported in U.S. Pat. No. 4,203,220. The preferred compound in said patent is 2-N'-allylamino-4,6-dichloro-1,3,5-triazine (IV):

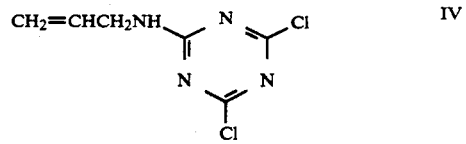

Organic esters of monofluorophosphoric acid having the formula (V):

wherein R is an unsaturated addition polymerizable group have been described as having good adhesion to hard tooth tissues in U.S. Pat. Nos. 3,882,600 and 3,997,504, although no indication regarding the adhesion to dentin of such esters of monofluorophosphoric acid is given in said patents.

In U.S. Pat. No. 3,629,187 there are described various adducts for use as dental resins, made by combining diglycidyl methacrylate of Bisphenol A (hereafter referred to as "BIS-GMA") and isocyanate or diisocyanate. Phosphorus-containing adducts are not described in said patent.

U.S. Pat. No. 2,674,590 describes various poly-condensation products in which phosphorus atoms are linked to two chain-forming aromatic esterifying groups and to one branched aromatic esterifying group containing a diphenyl group. U.S. Pat. No. 2,871,263 describes various phosphoric dihalides in which phosphorus is bonded to two halogen atoms, is doubly bonded to an oxygen atom, and is singly bonded to a monovalent aromatic hydrocarbon radical containing at least one olefinic double bond and having at least one halogen atom attached to a carbon atom therein. U.S. Pat. No. 4,030,933 describes phosphorus and halogen containing polymers prepared by reacting a halogenated derivative of bis(hydroxyethyl) terephthalate with a halogen-containing phosphorus monomer, the resulting polymer having repeating units in which halogen is not bonded directly to phosphorus.

A dentin adhesive composition should desirably offer good adhesion to both dentin and tooth enamel, as well as adhering well to other restorative and composite resins, crowns, and/or orthodontic brackets currently in use ("restorative" and "composite" will be used essentially interchangeably herein, in recognition of the fact that due to differing standards currently in effect throughout the world, an individual dental adhesive composition might be regarded as a "restorative" in some jurisdictions and as a "composite" in others). Also, a dentin adhesive composition should desirably reduce the need for detailed cavity preparation such as undercutting. In addition, a dentin adhesive coinposition should withstand repeated thermally-induced expansion and contraction while minimizing marginal leakage between the adhesive composition and adjacent tooth tissue or restorative or composite materials. Also, it would be desirable if a dentin adhesive composition offered sufficiently strong bonding to dentin and enamel that the acid etching technique currently used for most dental restorations could be eliminated.

DISCLOSURE OF INVENTION

The present invention provides, in one aspect, polymerizable compounds having particularly valuable use in dentistry, comprising an organic ester of one or more acids of phosphorus (hereafter referred to as "phosphorus acid esters" comprising the reaction product of a chlorine-containing or bromine-containing phosphorus acid with a polymerizable monomer having at least one reactive hydroxyl group. In another aspect, the present invention provides polymerizable compounds comprising a phosphorus acid ester, said ester), said ester having chlorine or bromine bonded alrectly to phosphorus, and the organic radical of said ester containing at least one polymerizable functional group. The present invention also provides a method for making such compounds.

In addition, the present invention provides dental liner compositions comprising at least one of said phosphorus acid esters together with at least one sulfur compound having sulfur in the $+2$ or $+4$ oxidation state, and optionally further comprising at least one tertiary amine, and at least one free-radical initiator, the resulting compositions being packaged in a stable, conveniently mixable configuration. This invention also provides dental compositions comprising at least one of said phosphorus acid esters together with at least one free-radical initiator or photoinitiator, said composition being bonded to a tooth. This invention also provides dental restorative, composite, or adhesive compositions comprising at least one of said phosphorus acid esters, at least one tertiary amine, at least one free-radical initiator, and optionally including at least one sulfur compound having sulfur in the $+2$ or $+4$ oxidation state, the resulting compositions being packaged in a stable, conveniently mixable configuration. Also, the present invention provides a method for using said liner, restorative, and composite compositions to repair or veneer hard dental tissue, and a method for applying orthodontic brackets or crowns to hard dental tissue using said adhesive compositions.

DETAILED DESCRIPTION

In the practice of the present invention, the preferred phosphorus acid esters are prepared by combining a chlorine-containing or bromine-containing phosphorus acid with BIS-GMA. Additional preferred phosphorus acid esters of the invention can be characterized by the formulas (VI) and (VII):

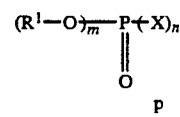

VI

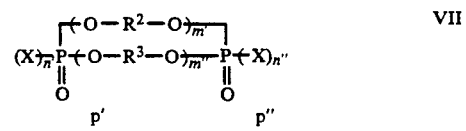

VII wherein
m is 1 to 3,
m' and m" are zero or 1 and are the same or different,
n is 1 to 4,
n' and n" are independently zero to 4 and are the same or different, with the proviso that n' and n" are both not zero,
p, p', and p" are zero or 1 and are the same or different,
m+n+2p=3 or 5,
m'+m"+n'+2p'=3 or 5,
m'+m"+n"+2p'=3 or 5,
$R^1$ is a monovalent olefinic organic radical (preferably alkenyl, cycloalkenyl, aralkenyl, or alkenaryl, having 2 to 40 carbon atoms) which can be straight chain, branched, or cyclic, can contain skeletal hetero atoms, i.e., atoms other than carbon (e.g., oxygen, sulfur, or non-basic nitrogen atoms), and can be unsubstituted or substituted with non-interfering moieties, e.g., moieties which do not interfere with free-radical polymerization of said phosphorus acid esters,
$R^2$ and $R^3$ are divalent olefinic organic radicals (preferably alkenylidene, oxyalkenylidene, cycloalkenylidene, arylenealkenylidene, or alkenylidenearylene, having 2 to 40 carbon atoms) which can be straight chain, branched, or cyclic, can contain skeletal hetero atoms, can be unsubstituted or substituted with non-interfering moieties, and are the same or different, and
X is Cl, Br, or $R^4$, where $R^4$, is an aliphatic or oxyaliphatic radical having 1 to 12 carbon atoms, and each X is the same as or different from other X, with the proviso that at least one X is Cl or Br.

Compounds of formula VI and VII contain trivalent or pentavalent phosphorus atoms. In compounds of formula VI, phosphorus is bonded to at least one chlorine or bromine atom. In compounds of formula VII, at least one phosphorus atom is bonded to at least one chlorine or bromine atom. Additional phosphorus acid esters of the invention can be characterized by the formulas $R^5OPOCl_2$, $(R^5O)_2POCl$ or $(R^5O)_3PO$ where $R^5O$ is the radical remaining after removal of a hydroxyl hydrogen atom from BIS-GMA. Preferably in compounds of this invention, phosphorus is bonded to chlorine. Preferably the phosphorus acid esters of this invention contain at least one double bond between phosphorus and oxygen or sulfur, with a double bond to oxygen being preferred. Most preferably two or more polymerizable functional groups per phosphorus atom are contained in the phosphorus acid esters of this invention. Also, the phosphorus acid esters of this invention are preferably liquids at room temperature.

The polymerizable functional group in the compounds of this invention is preferably a free-radically polymerizable group, such as an olefin, and is most preferably a monofunctional or difunctional acryl or methacryl radical. Other polymerizable functional groups include monofunctional or difunctional vinyl, allyl, crotyl, and cinnamyl radicals.

Representative compounds of useful in the present invention include:

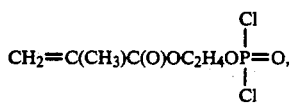

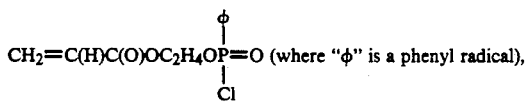

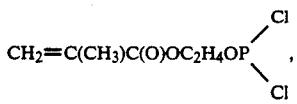

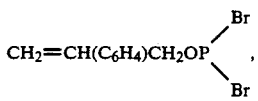

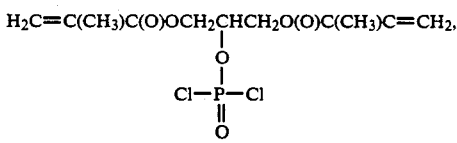

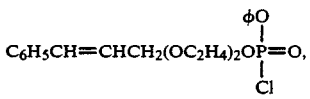

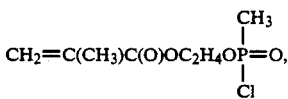

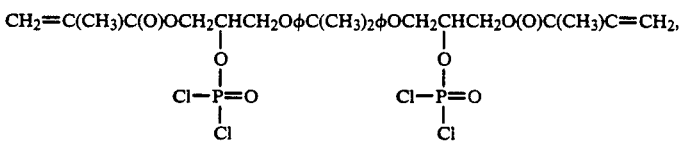

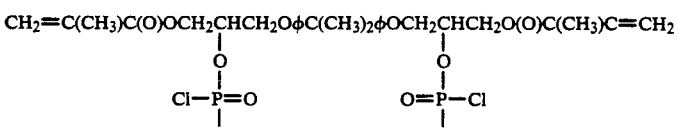

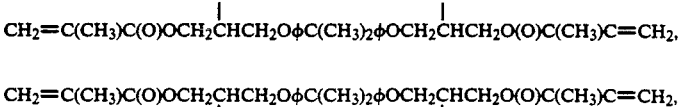

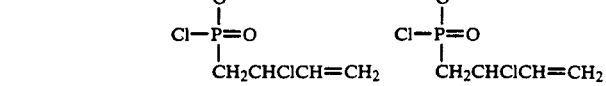

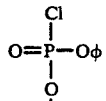
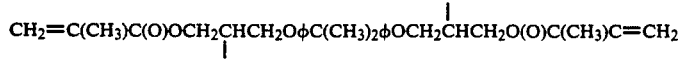
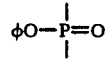
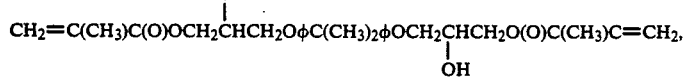
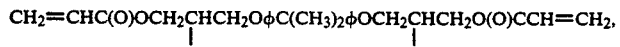

$CH_2=CHC(O)OCH_2CHCH_2O\phi C(CH_3)_2\phi OCH_2CHCH_2O(O)CCH=CH_2$,

$C_6H_5CH=CHCH_2CHC_3H_6CHCH_2CH=HCC_6H_5$,

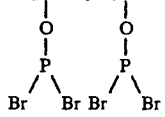

$H_2C=CHCH-O-HCCH=CH_2$, and

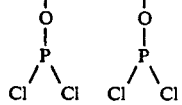

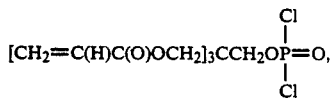

as well as mixtures of more than one of the above compounds.

The phosphorus acid esters of the invention can be used individually or in the form of adducts containing more than one phosphorus acid ester of the invention. Preferably, the phosphorus acid esters of the invention are prepared by combining a chlorine-containing bromine-containing phosphorus acid (e.g., phosphorus oxychloride, $POCl_3$, also known as phosphoryl chloride) with a polymerizable monomer having at least one reactive hydroxyl group (e.g., BIS-GMA). When the polymerizable monomer has a high initial viscosity, it is preferable to mix the phosphorus acid with the polymerizable monomer and a suitable diluent, e.g., triethyleneglycol dimethacrylate.

The phosphorus acid and polymerizable monomer having at least one hydroxyl group will react at low temperature, e.g., at room temperature, and the reaction mixture will increase in viscosity, preferably reaching an equilibrium state that is stable over time. The reaction product of such a mixture will generally be an adduct, the phosphorus acid esters of which are the product of reactions between some or all of the various hydroxyl groups of the polymerizable monomer and available chlorine or brown atoms of the phosphorus acid. Sufficient phosphorus acid should be added to the polymerizable monomer to provide good bonding and handling performance in liner, restorative, or composite compositions prepared therewith. For an adduct prepared by combining phosphorus oxychloride and BIS-GMA, about 0.25 to twenty percent by weight phosphorus oxychloride, and preferably about one to ten percent by weight phosphorus oxychloride should be used, based on the weight of BIS-GMA. Because BIS-GMA contains two hydroxyl groups per molecule, the above weight percentage values represent equivalent ratios Of $POCl_3$ to BIS-GMA of about 0.025:1 to 1:1, preferably about 0.05:1 to 0.5:1. Suitable adjustment of such equivalent ratios should be made when phosphorus acid esters of this invention are prepared from polymerizable monomers having other hydroxyl functionality, e.g., monofunctionality or trifunctionality. Also, suitable adjustment of such equivalent ratios should be made when phosphorus acid esters of this invention are prepared from phosphorus acids other than phosphorus oxychloride. Expressed in terms of the ratio of halogen atoms in the phosphorus acid to hydroxyl groups in the polymerizable monomer, the phosphorus acid and polymerizable monomer should be combined in a ratio of halogen atom to hydroxyl group between about 0.0375:1 to 1.5:1, preferably about 0.075:1 to 0.75:1.

If lesser amounts of phosphorus acid than those amounts sufficient to provide good bonding and handling performance are used, the resulting adduct may have low adhesion to dentin and enamel when polymerized therewith. If larger amounts of phosphorus acid than those sufficient to provide good bonding and handling are used, the resulting adduct will tend to homopolymerize, thereby having inadequate shelf life.

Other phosphorus acids which can be reacted with polymerizable monomers having reactive hydroxyl groups include $CH_3POCl_2$, $PCl_3$, $PCl_5$, $C_6H_5POCl_2$, $C_6H_5OPOCl_2$, and $PBr_3$. Such phosphorus acids can be used singly or in combination. Phosphorus oxychloride is a preferred phosphorus acid for use in the preparation of phosphorus acid esters of this invention.

Other polymerizable monomers having reactive hydroxyl groups which can be used in this invention include hydroxyethyl methacrylate, pentaerythritol triacrylate, glycerol dimethacrylate, methyl vinyl alcohol, vinyl benzyl alcohol, allyl alcohol, crotyl alcohol, and cinnamyl alcohol.

The mixing of phosphorus acid and polymerizable monomers having reactive hydroxyl groups can be carried out at room temperature. The attainment of equilibrium between the phosphorus acid and polymerizable monomer can be determined by observing the viscosity of the adduct over time, with equilibrium being indicated by a leveling off of such viscosity.

The adhesive strength, resistance to microleakage, and other characteristics of the phosphorus acid esters of this invention can be evaluated by forming a polymerizable composition containing such phosphorus acid esters together with a sulfur compound having sulfur in the $+2$ or $+4$ oxidation state (with "oxidation state" being defined according to Hendrickson et al, *Organic Chemistry*, 3d Ed., pp 796–799 (McGraw Hill Co., 1970)), a tertiary amine, and a free-radical initiator. The resulting composition is then tested for adhesive strength and resistance to micro-leakage, using the methods outlined in the examples below, and evaluated for toxicity (e.g., cytotoxicity to L-929 mouse fibroblasts) and for other desired characteristics (e.g., shelf life).

The liner compositions of the invention ordinarily contain sulfur in the $+2$ or $+4$ oxidation state which acts as activator, in amounts of about 0.5 to 10 percent by weight. Suitable activators are ordinarily alkali metal salts, such as potassium or sodium salts, or ammonium salts, of sulfur-containing anions such as sulfinate, sulfite, or sulfonate anions. Sodium benzene sulfinate is a preferred activator. Such activators can, if desired, be employed in restorative, composite, and adhesive compositions of this invention.

The liner, restorative, composite, and adhesive compositions of the invention typically contain a tertiary amine which acts as a polymerization accelerator, in amounts of about 0.5 to 10 percent by weight. Suitable tertiary amines include DHPT, N,N-dimethyl-para-toluidine, N,N-bis(2-hydroxyethyl)-3,5-xylidine, and the like. DHPT is a preferred tertiary amine. To a certain extent it is believed that the use of accelerator can be avoided in compositions of this invention if sufficient activator (i.e., a sulfur compound having sulfur in the $+2$ or $+4$ oxidation state) is substituted for such accelerator. Accordingly, the present invention includes compositions containing phosphorus acid ester, activator, and catalyst, as well as compositions containing accelerator in addition to such ingredients.

Liner, restorative, composite, and adhesive compositions of the invention-typically contain a polymerization catalyst in amounts of about 0.05 to 5 percent by weight. Suitable polymerization catalysts include free-radical initiators such as peroxides, e.g., benzoyl peroxide, acetyl peroxide, lauroyl peroxide, and t-butyl hydroperoxide. Benzoyl peroxide is a preferred catalyst. Photoinitiators (i.e., light-activatable catalysts) such as monoketals of aromatic 1,2-diketones or a combination of benzil and a dialkylamino acrylate or methacrylate can also be used.

When the compositions of the invention are used as liners which are then covered with polymerizable restorative or composite compositions, the liner composition need not contain accelerator or catalyst so long as sufficient accelerator or catalyst can migrate from the polymerizable restorative or composite composition into the liner composition, thereby promoting polymerization of the resin in the liner. However, for optimum reproducibility in use, liner compositions of this invention typically contain measured amounts of activator, accelerator, and catalyst.

Other adjuvants such as solvents, stabilizers, fillers, pigments, inhibitors, and the like can also be used in the compositions of this invention. The amounts and types of such adjuvants, and their manner of addition to the compositions of this invention will be essentially the same as currently used in existing liner, restorative, composite, or adhesive compositions familiar to those skilled in the art. Ethanol is a preferred solvent for use in liner compositions of this invention. Quartz, and glasses such as zinc glass or other radiopaque glass treated with appropriate silane surface treatment, are preferred fillers for use in restorative and composite compositions of this invention. Asbestos-free talc is a preferred filler for use in adhesive compositions of this invention.

The compositions of the invention can be put up in one-part or multiple-part packages. For example, one-part packages of liner compositions of the invention can be prepared by combining one or more of the above-described phosphorus acid esters with activator, accelerator, inhibitor, and light-activatable catalyst. The resulting mixture will remain in a stable, essentially uncured state until exposed to suitable radiation, e.g., actinic light radiation. Also, liner compositions of this invention can be prepared in one-part packages containing phosphorus acid ester and catalyst but omitting activator or accelerator, and relying on an adjacent layer of polymerizable restorative or composite to supply such omitted ingredient. The resulting composition will remain in a stable, uncured state until combined with the missing ingredient, e.g., activator migrating into the liner composition from an adjacent layer of polymerizable restorative or composite composition.

Multiple-part packages of liner compositions of this invention can be prepared, for example, by combining a suitable solvent (e.gi, ethanol), activator, and accelerator in a first part, and phosphorus acid ester and catalyst in a second part. While uncombined, the resulting two-part package will remain in a stable, uncured state. When the two parts are mixed together, e.g., by spatulation or other means, the resulting liner composition will rapidly cure. The amount of each ingredient in such two-part package should be adjusted to allow sufficient working time for the practitioner to mix and apply the liner composition as desired, together with attainment of the desired physical properties in the cured liner.

If desired, other combinations of phosphorus acid ester, activator, accelerator, catalyst, and any other desired adjuvants can also be employed in multiple-part packages of liner compositions of this invention. Preferably, a multiple-part liner composition package offers ease of mixing, good shelf life, and desirable physical properties after cure.

One-part packages of restorative, composite, and adhesive compositions of this invention can be prepared, for example, by combining one or more of the above-described phosphorus acid esters with accelerator, inhibitor, light-activatable catalyst, and filler. The resulting mixture will remain in a stable, essentially uncured state until exposed to suitable radiation, e.g., actinic light radiation.

Multiple-part packages of restorative, composite, and adhesive compositions of this invention can be prepared, for example, by combining a polymerizable resin (e.g., BIS-GMA), accelerator, and filler in a first part, and phosphorus acid ester, catalyst, and filler in a second part. While uncombined, the resulting two-part package will remain in a stable, uncured state. When the two parts are mixed together, e.g., by spatulation or other means, the resulting restorative, composite, or adhesive composition will rapidly cure. The amount of each ingredient in such two-part package should be adjusted to allow sufficient working time and attainment of desired physical properties.

If desired, other combinations of polymerizable resin, phosphorus acid ester, activator, accelerator, catalyst, filler, and any other desired adjuvants can also be employed in multiple-part packages of restorative, composite, and adhesive compositions of this invention, coincident with attainment of ease of mixing, good shelf life, and desirable physical properties after cure.

When used as liners, the compositions of this invention are applied in a manner similar to that used for existing dental liner compositions. However, cavity preparation is simplified. Excavation can be limited to the removal of damaged or defective tooth structure. Undercutting of the cavity is generally not required. If desired, acid etching of the cavity can be omitted. This invention therefore shortens the time required for completion of a dental restoration and reduces trauma to healthy tooth structure.

When used as a composite or restorative, the compositions of this invention are used in a fashion similar to that used for existing dental composites and restoratives. Preferably, where the compositions of this invention are used as composites or restoratives, they are used in conjunction with a liner prepared according to this invention which is applied to the excavated cavity prior to application of the composite or restorative composition.

When used as an orthodontic bracket adhesive, the compositions of this invention are preferably used as primers in conjunction with existing filled orthodontic bracket adhesives. The compositions of the invention can also be combined with fillers and used in place of such adhesives, preferably in conjunction with a liner prepared according to the present invention. Where desired, e.g., to obtain very high bonding strength, acid etching of the exposed tooth enamel can be employed. However, satisfactory results can often be obtained in the absence of such acid etching, thereby reducing damage to enamel.

The following examples are offered to aid understanding of the present invention and are not to be construed as limiting the scope thereof.

EXAMPLE 1

Preparation of Organic Ester of Phosphorous Oxychloride 10 g of phosphorus oxychloride was dissolved in a polymerizable monomer mixture containing 95 g of BIS-GMA, 2.0 g of benzoyl peroxide, 95 g of triethylene-glycol dimethacrylate, 0.13 g of butylated hydroxytoluene, 0.34 g of phenyl salicylate, and 0.24 g of glycidyl methacrylate. The resulting mixture was allowed to stand at room temperature for 5 days. During this time, the reaction mixture underwent a gradual increase in viscosity from about 200 cps to 1,345 cps, measured at 24° C. No further change in viscosity was apparent upon further standing. Infrared analysis of the resulting product established that the number of hydroxyl groups had diminished. The presence of carbonyl, phenyl, and phosphate groups was also established by IR spectrum analysis. Nuclear magnetic resonance spectroscopy established that the product contained a mixture of phosphate esters.

The above reaction product was used as the first part of a two-part liner composition. The second part of such liner composition was a solution of three percent by weight sodium benzene sulfinate and one percent by weight DHPT in ethanol. Adhesion of this liner composition to unetched dentin was evaluated using the following procedure. Four bovine teeth of similar age and appearance were partially embedded in circular acrylic disks. The exposed portion of each tooth was ground flat and parallel to the acrylic disk using 120 grit silicon carbide paper-backed abrasive mounted on a lapidary wheel, in order to expose the tooth dentin. During this and subsequent grinding and polishing steps, the teeth were continuously rinsed with water. Further grinding and polishing of the teeth was carried out by mounting 400 grit silicon carbide paper-backed abrasive, and 600 grit alumina rubber-backed abrasive on the lapidary wheel.

The teeth were then washed with distilled water using a "Water Pik" apparatus set on "hard" for 15 seconds, followed by drying with air. One drop of each part of the above two-part liner composition was placed on a mixing pad. The drops were mixed together by hand spatulation for about 5 seconds, painted onto the polished tooth surface, and blown into a thin film with compressed air. A previously prepared Teflon mold having a 5 mm diameter hole lined with a gelatin sleeve was clamped around the tooth so that the central axis of the hole in the mold was normal to the polished, liner-coated tooth surface. The cavity in the mold was filled with a standard, premixed dental composite ("Concise" brand, commercially available from 3M). The tooth and mold were allowed to stand for about 10 minutes at room temperature. The mold was then carefully removed from the tooth, leaving a button-like molded composite shape attached to the liner layer. The disk-tooth-liner-composite combination was stored in distilled water at 37° C. for 24 hours.

Adhesion of the liner composition to the polished, unetched bovine dentin was evaluated by placing the tooth mounting disk in a holder and clamping the holder in the jaws of an "Instron" apparatus with the liner layer parallel to the direction of pull. A loop of orthodontic wire (0.44 mm diameter) was placed around the composite button adjacent to the polished tooth surface. The ends of the orthodontic wire were clamped in the pulling jaws of the Instron apparatus, thereby placing the liner bond in shear stress. At a crosshead speed of 5 mm/min, the average measured shear strength of the liner-dentin bond was 51 kg/cm$^2$. If allowed to stand in 37° C. distilled water for 42 hours (instead of 24 hours), the average measured strength of the liner-dentin bond was 60 kg/cm$^2$.

Using the above technique, the liner bond strength on polished bovine enamel was also evaluated, both with and without acid etching for 1 minute with 37% orthophosphoric acid. Bond strength on acid etched enamel was an average 370 kg/cm$^2$, and bond strength on unetched enamel was an average of 120 kg/cm$^2$.

The above-described liner composition was also evaluated for resistance to thermal cycling. Six samples of the liner composition on unetched dentin, and six samples on unetched enamel, prepared as described above, were thermally cycled between 12° and 46° C. for 500 cycles. Adhesion values were then measured as described above. After cycling, the average liner bond strength on unetched dentin was 40 kg/cm$^2$, and the average liner bond strength on unetched enamel was 88 kg/cm$^2$.

In a comparison run, "Clearfil" liner (commercially available from the Kuraray Co.1 Ltd.) was similarly evaluated. The initial average bond strength of "Clearfil" liner was 26 kg/cm$^2$ on unetched dentin, 200 kg/cm$^2$ on etched enamel, and 50 kg/cm$^2$ on unetched enamel. After thermal cycling as described above, the average bond strength of "Clearfil" liner was 13 kg/cm$^2$ on unetched dentin and 21 kg/cm$^2$ on unetched enamel.

EXAMPLE 2

Shelf Stability

The composition of the invention shown in Example 1 was stored at 45° C. for 4 weeks. When the stored composition was mixed and tested as in Example 1, the initial average liner bond strength values were within 0.3 kg/cm$^2$ of the average values of Example 1.

EXAMPLES 3-26

Adhesion Value of Other Compositions of Invention to Unetched Dentin

Using the method of Example 1, different types and amounts of phosphorus acids were combined with the polymerizable monomer mixture. Set out below in Table 1 are the example number, phosphorus acid used to form the organic ester, the weight percent of such acid added to the polymerizable monomer mixture of Example 1, and the bond strengths of the resulting liner compositions when applied to unetched dentin.

TABLE I

| Example Number | Phosphorus Acid | Weight Percent | Bond strength Kg/cm$^2$ |
|---|---|---|---|
| 3 | POCl$_3$ | 0.1 | 3 |
| 4 | POCl$_3$ | 0.25 | 30 |
| 5 | POCl$_3$ | 0.5 | 54 |
| 6 | POCl$_3$ | 1.0 | 43 |
| 7 | POCl$_3$ | 1.5 | 48 |
| 8 | POCl$_3$ | 2.0 | 58 |
| 9 | POCl$_3$ | 2.5 | 53 |
| 10 | POCl$_3$ | 3.0 | 45 |
| 11 | POCl$_3$ | 3.5 | 48 |
| 12 | POCl$_3$ | 4.0 | 51 |
| 13 | POCl$_3$ | 4.5 | 45 |
| 14 | POCl$_3$ | 6.0 | 43 |
| 15 | POCl$_3$ | 6.5 | 35 |
| 16 | POCl$_3$ | 7.5 | 27 |
| 17 | POCl$_3$ | 8.0 | 25 |
| 18 | POCl$_3$ | 8.5 | 31 |
| 19 | POCl$_3$ | 9.1 | 25 |
| 20 | POCl$_3$ | 10 | 26 |
| 21 | C$_6$H$_5$POCl$_2$ | 5 | 10 |
| 22 | C$_6$H$_5$OPOCl$_2$ | 5 | 40 |

TABLE I-continued

| Example Number | Phosphorus Acid | Weight Percent | Bond strength Kg/cm$^2$ |
|---|---|---|---|
| 23 | PCl$_3$ | 2.5 | 30 |
| 24 | PCl$_3$ | 5 | 39 |
| 25 | PCl$_5$ | 5 | 16 |
| 26 | PBr$_3$ | 2.5 | 42 |

EXAMPLE 27

Using the method of Example 1, a two-part liner composition was prepared. The first part of the liner composition was prepared by mixing 0.5 g POCl$_3$, 0.12 g benzoyl peroxide, and 9.5 g pentaerythritol triacrylate. The second part of the liner composition was a solution of three percent by weight sodium benzene sulfinate and one percent by weight DHPT in ethanol. The composition was evaluated as in Example 1, and had an average shear strength on unetched dentin of 17 kg/cm$^2$.

EXAMPLE 28

Using the method of Example 27, a two-part liner composition was prepared, using a mixture of 0.5 g of POCl$_3$, 0.057 g benzoyl peroxide, 0.0095 g Bisphenol A, 0.0029 g butylated hydroxytoluene, 4.68 g triethyleneglycol dimethacrylate, and 4.75 g pentaerythritol triacrylate. The average shear strength of the polymerized resin was 12 kg/cm$^2$.

EXAMPLE 29

A two-part liner composition containing a monofunctional methacrylate was prepared. The first part of the liner composition was prepared by adding 38.3 g (0.25 moles) POCl$_3$ to a stirred, ice-cooled solution of 25.3 g triethylamine (0.25 moles) in 80 ml tetrahydrofuran and 60 ml ether. To the resulting mixture was added dropwise 32.5 g (0.25 moles) 2-hydroxyethyl methacrylate. The reaction mixture was stirred for about 2 hours, filtered, and the filter cake washed with ether. The resulting red colored filtrate was concentrated to yield an oil weighing 60.5 g and having the formula:

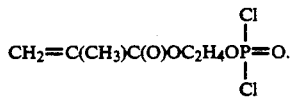

A 5 g portion of this oil was added to a mixture of 98.54 g triethyleneglycol dimethacrylate, 0.062 g butylated hydroxytoluene, 0.2 g Bisphenol A, and 1.2 g benzoyl peroxide.

The second part of the liner composition was a solution of three percent by weight sodium benzene sulfinate and one percent by weight DHPT in ethanol. The composition was evaluated as in Example 1, and had an average shear strength on unetched dentin of 5 kg/cm$^2$.

EXAMPLE 30

Example 29 was repeated using 0.15 moles POCl$_3$, 0.30 moles triethylamine, and 0.30 moles 2-hydroxyethyl methacrylate, thereby producing the compound:

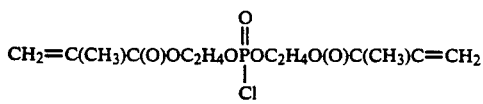

A liner composition prepared and evaluated as in Example 29 had an average shear strength on unetched dentin of 9 kg/cm².

EXAMPLE 31

The liner compositions of the invention shown in Examples 1, 9, 16, and 19 were used as primers for orthodontic bracket adhesives. The resins were mixed and applied to tooth enamel which had been previously polished with 600 grit silicon carbide paper-backed abrasive, washed with a "Water Pik", and air-dried. A layer of standard orthodontic bracket adhesive ("Concise 1960" brand, commercially available from 3M) was applied to the back of an orthodonic bracket and pad (Bracket No. 007 and pad Pad No. 065, commercially available from American Orthodontics, Inc.). The adhesive-coated pad was applied to the primer and the resulting assembly allowed to cure for ten minutes at room temperature. The cured assemblies were stored in water at 37° C. for 24 hours and then evaluated for average shear strength using the "Instron" apparatus described in Example 1. The results are shown below.

| Primer, from resin of Example | Average Shear Strength Kg/cm² |
| --- | --- |
| 1 | 88 |
| 9 | 85 |
| 16 | 91 |
| 19 | 78 |

In a comparison run, standard "Enamel Bond" primer from the "Concise 1960" kit was used in place of the above primers. The average shear strength was 31 kg/cm². Acid etching for one minute with 37% orthophosphoric acid increased the average shear strength using "Enamel Bond38 primer to 125 kg/cm².

This example shows that the compositions of this invention can be used as primers in conjunction with a standard orthodontic bracket adhesive, to provide very high average shear strengths without the use of acid etching.

COMPARATIVE EXAMPLE 1

An organic ester of monofluorophosphoric acid described in U.S. Pat. No. 3,997,504 was prepared as described in said patent, and then evaluated for adhesion to dentin as in Example 1.

Pure difluorophosphoric acid was obtained following the procedure of P. A. Bernstein et al, *Inorg. Chem.* 10, 1549 (1971), by cooling 87.4 g of impure difluorophosphoric acid to 0° C. The cooled acid was slowly added to a flask made of "Monel" metal, containing 38 g of P₂O₅. The resulting mixture was allowed to stand with occasional shaking for 1 hour at 0° C. The mixture was then slowly pumped through a trap cooled to −78° C. with acetone and "Dry Ice". After about 1.5 hours, 13 g of pure diiuorophosphoric acid was collected. The pure acid was a clear, fuming liquid.

A 4.8 g portion of pure difluorophosphoric acid was mixed dropwise with 4.0 g 2-hydroxyethyl methacrylate, and allowed to react overnight at room temperature under a dry nitrogen flush. The product, methacryloxyethyl monofluorophosphate, was vacuum distilled to remove any excess difluorophosphoric acid. The residue was filtered through glass wool and collected.

Next, a liner composition was prepared from the following ingredients:

| Ingredient | Amount, g |
| --- | --- |
| A. Bis(2-methacryloxyethyl)isophthalate | 2.35 |
| Bis(2-methacryloxyethyl)phthalate | 1.90 |
| Bis(2-methacryloxyethyl)terephthalate | 0.75 |
| Methyl methacrylate | 0.5 |
| Dodecyl mercaptan | 0.025 |
| Methacrylic acid | 0.015 |
| 2,6-di-tertiary butyl p-cresol | 0.01 |
| N,N-dimethyl-3,5-dimethylaniline | 0.035 |
| Dimethylpolysiloxane | trace |
| Methacryloxyethyl monofluorophosphate | 0.5 |
| Gamma-methacrylpropyltrimethoxysilane | 0.025 |
| B. Acetone | 3.4 |
| Chloroform | 1.7 |
| Benzoyl peroxide | 0.06 |

The above liner composition was evaluated using the method of Example 1. The average shear strength of the polymerized composition was 15.6 kg/cm² on unetched dentin, and 6 kg/cm² on unetched enamel.

COMPARATIVE EXAMPLE 2

Using the method of Example 1, 5 percent by weight pure difluorophosphoric acid was added to the polymerizable monomer mixture of Example 1, and allowed to stand for 5 days. The resulting adduct was then evaluated as in Example 1. The polymerized resin had an average shear strength of 20 kg/cm².

If allowed to stand in 37° C. distilled water for 42 hours (instead of 24 hours) as in Example 1, the polymerized resin had an average shear strength of 29 kg/cm².

This Example shows that use of a

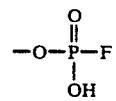

moiety in an adduct with the difunctional methacrylate BIS-GMA gave lower average shear strength values than corresponding BIS-GMA adducts containing moieties such as

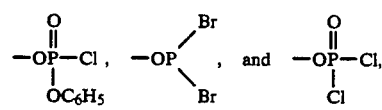

and derived by the addition to BIS-MA of 5% by weight of phosphorus acids such as C₆H₅OP(O)Cl₂, PBr₃, or POCl₃.

Various modifications and alterations of this invention will become apparent to those skilled in the art without departing from the scope and spirit of this invention, and it should be understood that this invention is not limited to the illustrative embodiments set forth herein.

What is claimed is:

1. An adhesive which comprises a polymerizable composition consisting of (a) 1 part by weight of a monomer represented by the formula

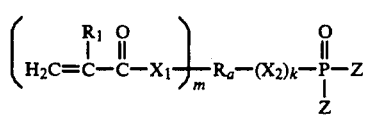

where $R_1$ denotes H or $CH_3$; $R_a$ denotes a $C_{6-40}$ organic residue having a valence of m+1; $X_1$ and $X_2$ denote O, S or NR', (where R' denotes H or a $C_{1-6}$ hydrocarbon group), two of $X_1$ may be different from each other when m is 2; z denotes a halogen; and m is 1 or 2 and k is 0 or 1, and (b) up to 199 parts by weight of a monomer selected from the group consisting of mono-, di-, tri-, and tetrafunctional (meth)acrylates, styrene, divinyl benzene, p-chloro-styrene, (meth)acrylamide or derivatives thereof, N-(hydroxymethyl)acrylamide, (meth)acrylic acid, isobutylvinyl ether, vinyl acetate, diethyl fumarate, diethyl maleate, maleic anhydride, methyl vinyl ketone, allyl chloride, vinyl naphthalene and vinylpyridine or combinations thereof.

2. An adhesive which comprises a polymerizable composition consisting of (a) a monomer represented by the formula

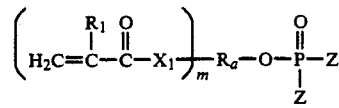

where $R_1$ denotes H or $CH_3$; $R_a$ denotes a $C_{3-37}$ organic residue having a valence of M+1; $X_1$ denotes O, S or non-basic N; Z denotes Cl or Br; and m is 1 or 2, and (b) a monomer selected from the group consisting of mono- and difunctional (meth)acrylates or combinations thereof.

3. An adhesive as set forth in claim 2, wherein m is 1.

4. An adhesive as set forth in claim 2, wherein m is 1, and $X_1$ is —O—.

5. An adhesive as set forth in claim 2, wherein a curing agent is incorporated in an amount of 0.05 to 5 parts by weight for 100 parts by weight of the polymerizable monomers.

6. An adhesive as set forth in claim 5, wherein the curing agent is a redox type polymerization initiator.

7. An adhesive as set forth in claim 5, wherein the curing agent is a photoinitiator.

8. An adhesive as set forth in claim 2, wherein a volatile organic solvent is incorporated in the polymerizable monomers.

9. An adhesive as set forth in claim 2, wherein a filler is incorporated in the polymerizable monomers.

* * * * *

UNITED STATES PATENT AND TRADEMARK OFFICE
CERTIFICATE OF CORRECTION

PATENT NO.:    5,304,585                                         Page 1 of 2

DATED:         April 19, 1994

INVENTOR(S):   James E. Bunker

It is certified that error appears in the above-identified patent and that said Letters Patent is hereby corrected as shown below:

Cover page item, [57], line 8, delete "line" and insert --liner--.

Column 4, lines 12-15 delete "

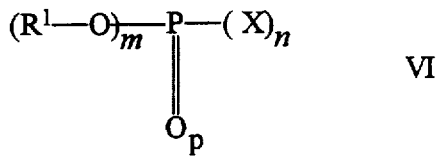

and insert --

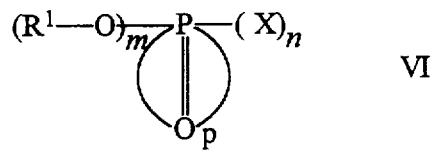

Column 4, line 35, delete " m' +m" +n" +2p' = 3 or 5 " and insert -- m' +m" +n" +2p" = 3 or 5--

Column 7, line 62, delete "brown" and insert --bromine--.

Column 10, line 51, delete "(e.gi, ethanol), and insert --e.g., ethanol),--.

UNITED STATES PATENT AND TRADEMARK OFFICE
CERTIFICATE OF CORRECTION

PATENT NO. : 5,304,585
DATED : April 19, 1994
INVENTOR(S) : James E. Bunker

It is certified that error appears in the above-indentified patent and that said Letters Patent is hereby corrected as shown below:

Column 13, line 20, delete "Co.1" and insert --Co.,--.

Signed and Sealed this

Fourth Day of June, 1996

*Attest:*

BRUCE LEHMAN

*Attesting Officer*     *Commissioner of Patents and Trademarks*